United States Patent [19]

Mack

[11] Patent Number: 5,097,881
[45] Date of Patent: Mar. 24, 1992

[54] ULTRASONIC LOG GRADING

[75] Inventor: Michael J. Mack, Waterloo, Iowa

[73] Assignee: Blount, Inc., Montgomery, Ala.

[21] Appl. No.: 691,749

[22] Filed: Apr. 25, 1991

[51] Int. Cl.$^5$ ............................ B27L 1/00; B27B 1/00
[52] U.S. Cl. ................................. 144/356; 73/622;
73/629; 83/364; 83/370; 144/3 N; 144/2 Z;
144/343; 364/559; 427/284
[58] Field of Search ............... 83/364, 370; 73/619,
73/622, 629; 144/2 R, 3 R, 3 N, 2 Z, 34 R, 3 D,
356, 343; 427/284; 364/559

[56] References Cited

U.S. PATENT DOCUMENTS

| | | | |
|---|---|---|---|
| 3,554,249 | 1/1971 | Vasteras et al. | 144/312 |
| 3,722,263 | 3/1973 | Hautaniemi et al. | 73/622 |
| 3,759,384 | 9/1973 | Holmberg et al. | 209/122 |
| 4,023,605 | 5/1977 | Hellstrom et al. | 144/312 |
| 4,027,528 | 6/1977 | Tyree | 73/67.85 |
| 4,099,420 | 7/1978 | Stouffer et al. | 73/629 |
| 4,149,089 | 4/1979 | Idelsohn et al. | 250/563 |
| 4,169,173 | 9/1979 | Bergholm et al. | 427/284 |
| 4,207,472 | 6/1980 | Idelsohn et al. | 250/563 |
| 4,356,850 | 11/1982 | Halgrimson et al. | 144/209 R |
| 4,412,297 | 10/1983 | Halgrimson et al. | 364/559 |
| 4,785,817 | 11/1988 | Stouffer | 128/660.07 |

Primary Examiner—W. Donald Bray
Attorney, Agent, or Firm—Klarquist, Sparkman, Campbell, Leigh & Whinston

[57] ABSTRACT

A log harvesting system is disclosed in which the log is graded automatically in the field by ultrasonic testing of the log. Pulses of utlrasonic waves are transmitted into the log to detect internal defects within the log by measuring changes in the transient time of the ultrasonic wave pulses through at least a portion of the log. A computer is used to determine the grade of the log and produce a grade output signal from transient time data and signals related to the length and diameter of the log. The log is marked with a different colored paint to indicate its grade by an automatic marking device in response to the receipt of the grade output signal. Ultrasonic testing apparatus may be added to a tree harvesting head with a saw for felling the tree and cutting the log to the proper length and delimber knives for removing limbs, in order to test the log for defects as the log is conveyed through such head. In one embodiment, a pair of ultrasonic transducer wheels are mounted on opposite sides of the log and pairs of transmitting and receiving transducers are selectively coupled to the log through liquid coupling chambers provided on the outer surface of such wheels as the wheels rotate along the length of the log.

30 Claims, 4 Drawing Sheets

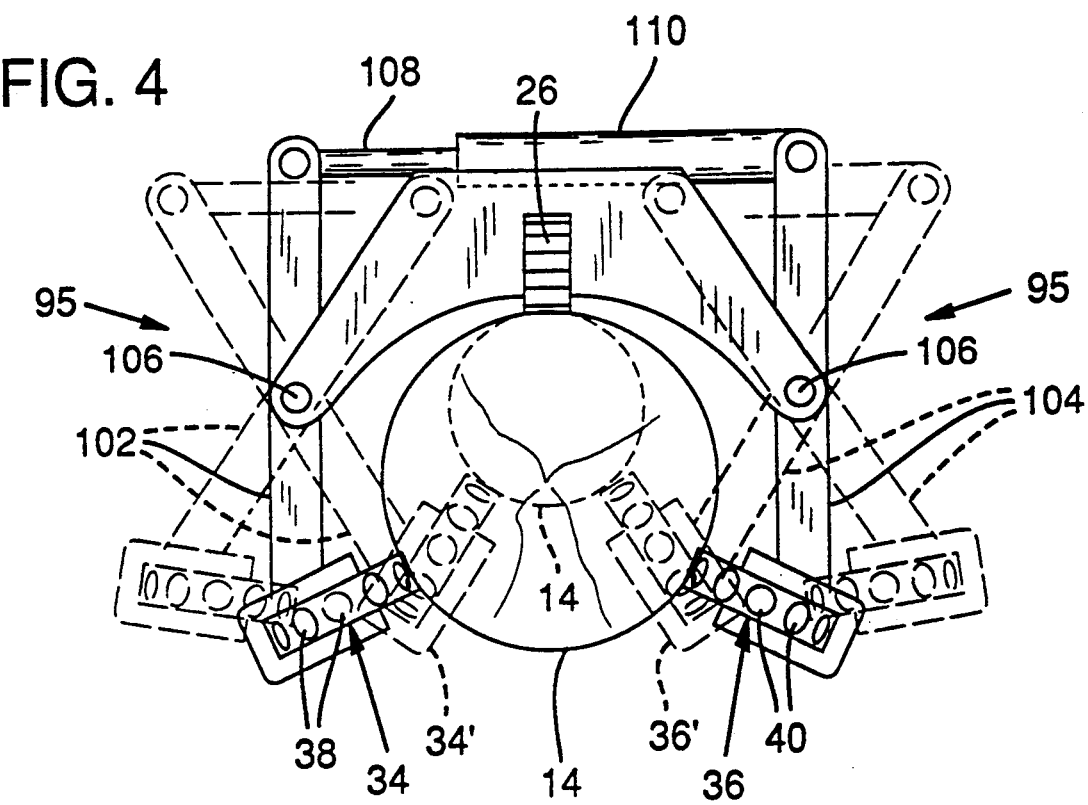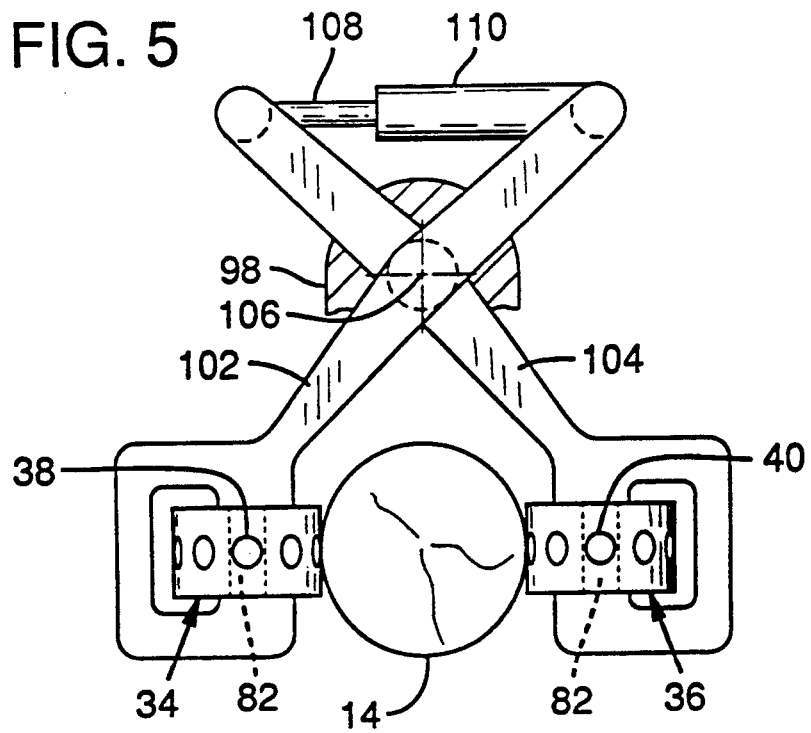

ULTRASONIC LOG GRADING

The present invention relates to the harvesting and grading of logs and in particular to log grading by ultrasonic testing of logs with pulses of ultrasonic waves to detect defects in the logs.

BACKGROUND OF THE INVENTION

Conventionally, logs have been graded primarily by visual inspection of the logs by an inspector who assigns a grade to the log based upon how the log appears to him. This log grading is highly subjective depending on the skill of the inspector and is prone to error. The present invention provides an automatic log grading technique using ultrasonic testing which detects internal defects within the log that cannot be seen visually and is therefore more accurate that visual inspection log grading.

Previously, the distance to a log has been determined by using ultrasonic waves to measure the diameter of the log at several longitudinal positions along the log in order to determine the optimum yield axis of the log for a veneer lathe or sawmill. In this regard see U.S. Pat. No. 4,356,850 of Halgrimson, et al., issued Nov. 2, 1982, and U.S. Pat. No. 4,412,297 of Halgrimson, et al., issued Oct. 25, 1983. However, in these prior methods sound waves are transmitted through the air and reflected off the surface of the log to the ultrasonic transducer from which they were emitted and sound waves are not transmitted through the log to determine internal defects in the manner of the present invention.

Previously it has been proposed to provide mechanical sensor means in the form of wheels which engage the log to determine the length and diameter of the log for automatic grading purposes using a computer as shown in U.S. Pat. 3,554,249 of Vasteras, et al., issued Jan. 12, 1971. However, unlike the present invention, this grading apparatus does not employ ultrasonic testing for detecting internal defects within the log and grading the log based upon such tests.

It has also been proposed to grade lumber by visual observation of a grader who looks at the surface of the lumber, as disclosed in U.S. Pat. No. 4,023,605 of Hellstrom, et al., issued May 17, 1977, and U.S. Pat. No. 3,759,384 of Holmberg, et al., issued Sept. 18, 1973. In addition, lumber has been inspected automatically by light scanning to determine surface defects as shown in U.S. Pat. No. 4,207,472 of Idelsohn, et al., issued June 10, 1980, and U.S. Pat. No. 4,149,089 of Idelsohn, et al., issued Apr/ 10, 1979. However, none of these patents disclose the use of ultrasonic sound waves transmitted through the interior of the log to detect internal defects in order to provide more accurate grading of the log in the manner of the present invention.

It has previously been proposed in U.S. Pat. No. 4,169,173 of Bergholm, et al., issued Sept. 25, 1979, to color mark logs to indicated their length, by automatically controlled paint sprayers. However, this patent does not deal with ultrasonic grading of logs and color marking them in accordance with the grade so determined, in the manner of the present invention.

In the unrelated field of the grading of meat, such as hog carcasses, such grading has been done by using ultrasonic testing to determine the fat thickness, as shown in U.S. Pat. No. 4,785,817 of Stouffer, issued Nov. 22, 1988, U.S. Pat. No. 3,722,263 of Hautaniemi, et al., issued Mar. 27, 1973 and U.S. Pat. No. 4,099,420 of Stouffer, et al., issued July 11, 1978. In this latter patent a fluid couplant is employed to couple the transducer to the surface of the body of the animal carcass. However, unlike the ultrasonic log grader apparatus of the present invention, this patent employs a closed chamber for the fluid couplant and slides the transducer and such chamber along the surface of the animal carcass, which is only possible because of the soft, smooth surface of such carcass Also of interest is U.S. Pat. No. 4,027,528 of Tyree, issued June 7, 1977, which shows liquid coupling for an ultrasonic transducer used in inspecting metal wall members such as steel tanks, ship hulls, and the like.

Previously it has also been proposed, in a research laboratory, to detect defects in lumber by submerging the lumber in a water tank and transmitting ultrasonic waves through the water into the lumber. This is not commercially practical for grading logs in the field immediately after the logs are cut.

SUMMARY OF INVENTION

The ultrasonic log grading system of the present invention employs one or more transducer wheels having a plurality of ultrasonic transducers mounted thereon, adjacent liquid coupling chambers formed on the outside surface of such wheels with sharpened outer edges for embedding into the surface of the log to close the coupling chamber, as the transducer wheel is rolled along the surface of the log when such log is conveyed through the delimbing knives of a tree harvesting head. This harvesting head is equipped with a chain saw for felling the tree and for cutting the log to the proper length after the log is conveyed through a delimbing knives in the harvester head and is measured for length and diameter by measuring wheels which contact the log. The harvesting head contains motor driven conveying wheels which have sharpened spikes for engaging the log and conveying it through the delimbing knives and through the transducer wheels for measurement of internal defects in the log by ultrasonic sound waves transmitted into the log through the coupling liquid.

A digital computer microprocessor is employed to automatically determine the grade of the log by processing data corresponding to the electrical signals of the ultrasonic transducers which indicate changes in density or acoustic impedance of the log due to internal defects, such as knots, detected within the log. It should be noted that these knot defects are of higher density than the surrounding wood so that the sound waves travel faster through such defects. Thus, the transient time of the sound wave through the log is an indication of the quality of the log. Data corresponding to such transient time is fed into the computer. At the same time electrical signals corresponding to the length and the diameter of the log being tested are also fed into the computer which computes the volume of the log and uses that, together with the ultrasonic transient time data, to determine the grade of the log. After the grade of the log is determined, color coded paint is sprayed on the end of the log to indicate its grade by an automatic paint spraying device activated by the computer.

The ultrasonic log grader system of the present invention has the advantage that it senses external and internal defects of the log and uses that information to automatically determine the grade of the log, which is more accurate than visual inspection of the log surface. In addition, the log is automatically graded in the field shortly after cutting the tree from which the log is taken. This is achieved by ultrasonic testing of the log as it is conveyed through the harvester head for delimbing and cutting to length. Such automatic grading in the field enables the log to be quickly sorted and loaded into trucks for distribution to the sawmill, veneer mill or paper pulp mill. In addition, by providing an ultrasonic coupling liquid such as water or water containing antifreeze for low temperature applications, in a coupling chamber provided on the outside surface of the transducer wheel between each transducer and the log as such log is conveyed through the harvesting head, a practical ultrasonic test system is provided for use in the field where the logs are harvested. This ultrasonic test system is not only practical and relatively inexpensive, but is fast and extremely accurate in grading the logs.

OBJECTS OF THE INVENTION

It is therefore one object of the present invention to provide an improved log grading system which uses ultrasonic testing to detect internal defects within the log in order to automatically grade the log more accurately.

Another object of the invention is to provide an improved ultrasonic log grading system in which the ultrasonic test apparatus is combined with a tree harvesting and delimbing apparatus to enable ultrasonic log grading in the field in a fast, efficient and accurate manner.

A further object of the invention is to provide such an ultrasonic log grading system in which one or more transducer wheels each having a plurality of ultrasonic transducers mounted about the periphery thereof are employed in a harvesting head to contact the log as it is conveyed past the transducer wheel in order to measure internal defects along the entire length of the log in a fast and relatively inexpensive manner.

An additional object of the invention is to provide such an improved ultrasonic log grading system in which the transducer wheel is provided with a liquid coupling chamber adjacent the outer end of each ultrasonic transducer in order to couple the sound waves between such transducer and the log through the coupling liquid in an efficient manner to enable ultrasonic grading of the log.

Still another object of the invention is to provide such an ultrasonic log grading system in which the test signals produced by the ultrasonic receiver transducers are used to determine the transient time of the sonic waves through the log and produce corresponding data which together with signals representing the length and diameter of the log is processed by a computer in order to produce an output grade signal indicating the grade of the log in a fast accurate manner.

A still further object of the present invention is to provide such an ultrasonic log grader system in which a color coding device is employed for indicating the grade of the log by marking a different color indication for each grade on such log automatically in response to the grade signal produced by the computer.

A still additional object of the invention is to provide a method of grading logs using ultrasonic waves to detect internal defects in the log by measuring the transient time of the sound wave through the log in order to measure changes in the acoustical impedance or density of the log caused by such defects as such log is scanned along its entire length by the ultrasonic transducer means.

DRAWINGS

Other objects and advantages of the present invention will be apparent from the following detailed description of certain preferred embodiments thereof and from the attached drawings of which:

FIG. 4 is a vertical section view taken along the line 4—4 of FIG. 3; and

FIG. 5 is a vertical section view of a second embodiment of an ultrasonic log grader system in accordance with the present invention, similar to that of FIGS. 3 and 4, but with a different support mechanism for the transducer wheels.

DESCRIPTION OF PREFERRED EMBODIMENTS

Figure 1:
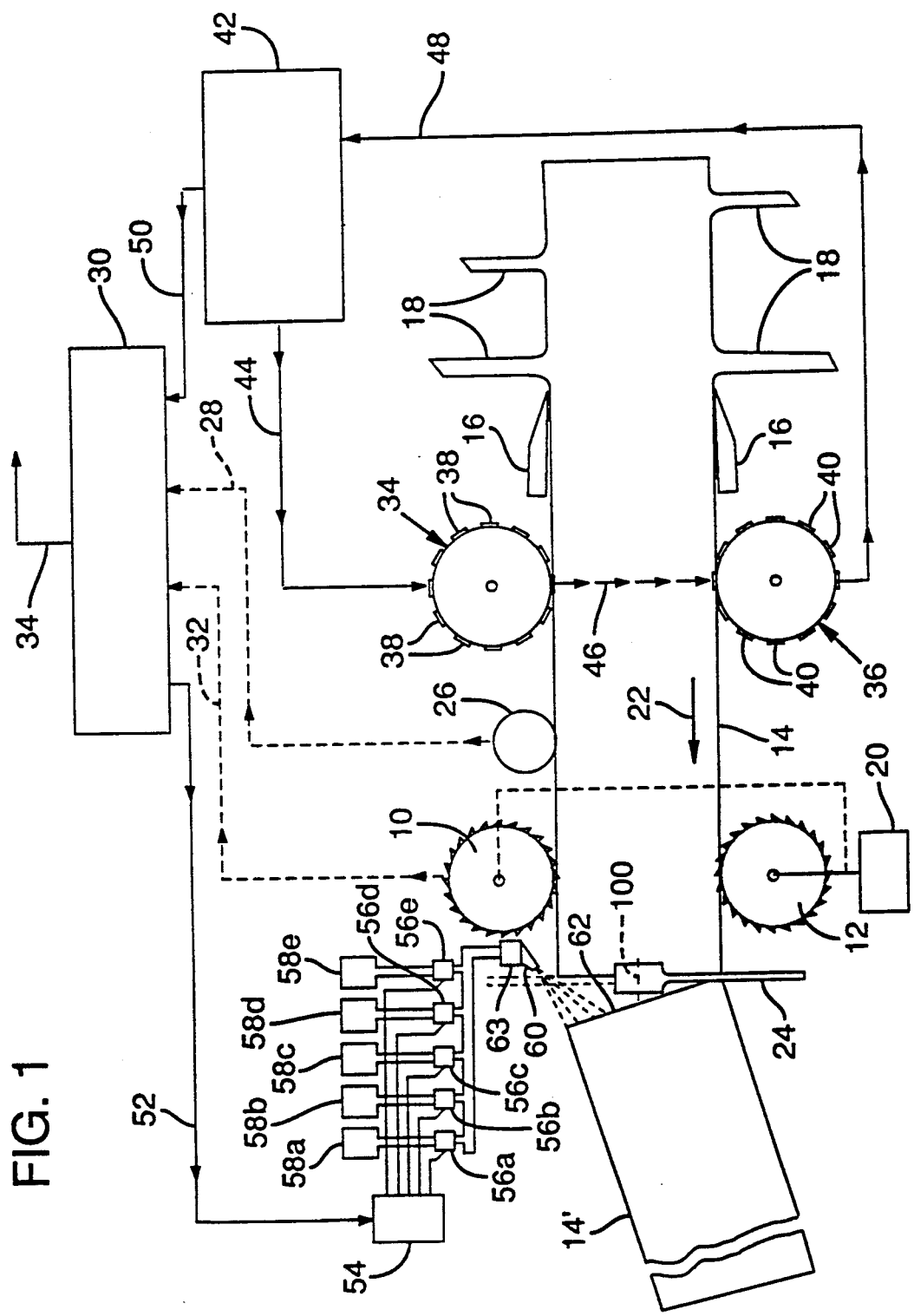
FIG. 1 is a schematic diagram showing an ultrasonic log grading system in accordance with on embodiment of the present invention which is incorporated as part of a harvesting head for cutting the log and delimbing such log.

As shown in FIG. 1, one embodiment of the present invention includes a pair of drive wheels 10, 12 with spiked outer surfaces which engage the opposite sides of a log 14 for conveying such log through a harvester head containing such drive wheels and delimbing knives 16 for removing the limbs 18 from such log. The drive shafts of the drive wheels 10 and 12 are both coupled to a hydrostatic motor 20 which rotates such wheels in a direction to convey the log to the left in the direction of arrow 22. A chain saw 24 is mounted on the harvesting head and is used to cut the tree down after it is engaged by the harvesting head and to cut the resulting log to the proper length. Thus, the chain saw 24 pivots into position to cut the rear end 62 of the log after it has been delimbed and advanced through the harvesting head as shown by the preceding log 14'.

The harvesting head includes at least one idler roll 26 which contacts the side of the log 14 and rotates along the log as it is conveyed past the idler roll to produce an electrical signal corresponding to the length of the log. The log length signal is produced by means of a shaft encoder connected to the idler roll which produces a digital output signal corresponding to the rotational position of the shaft of such idler roll. This log length signal may be supplied to one input terminal 28 of a digital computer 30. Another input 32 of the computer is connected to a log diameter signal output device coupled to the drive wheels 10 and 12 for indicating the spacing between such drive wheels which of course corresponds to the diameter of the log. The computer 30 processes the signals at inputs 28, 32 to determine the volume of wood in the log and stores such log volume signal in the computer memory. The computer supplies a corresponding log volume signal from a computer output 34 to a suitable analog display device or recorder.

An ultrasonic log grader system in accordance with the present invention includes a pair of spaced-apart transducer wheels 34, 36 which are mounted on the harvester head for movement into engagement with the outer surface of the log 14. The transducer wheels 34, 36 may each be mounted on a common support attached to one of the drive wheels 10, 12 in a manner hereafter described. Each of the transducer wheels 34, 36 has mounted on its periphery a plurality of ultrasonic transducers, such as piezoelectric transducers, including transmission transducers 38 on transducer wheel 34 and receiving transducers 40 on transducer wheel 36. These transducers are selectively connected by rotary switches to an ultrasonic pulser and time interval measurement circuit 42 in a manner hereafter described. The transmitting transducers 38 mounted on transducer wheel 34 are connected to a voltage pulse output terminal 44 of the ultrasonic pulser and time interval measurement circuit 42. The ultrasonic pulser and time interval measurement circuit 42 produces an output voltage pulse on output 44 that is applied to a selected one of the transmitting transducers 38 which is in engagement with the log 14 in order to cause such transducer to emit an ultrasonic sound wave. The ultrasonic wave passes in the direction of arrows 46 from the transmitting transducer 38 through such log to a selected one of the receiving transducers 40 on the transducer wheel 36 which is in engagement with the log at that time. The ultrasonic wave 46 transmitted through the log 14 is delayed in the log an amount of time determined by the acoustical impedance of the portion of the log in the path of such sound wave before it is received by the selected receiver transducer 40. Such acoustical impedance is determined by the density of the wood in such log and defects in the log, such as knots, change such density which affects the speed that the ultrasonic wave traverses the log. Thus, the transient time of the sound wave through the log corresponds to the density of the log which for a known species of wood indicates the extent of defects in the log so that it can be graded. The receiver transducer receiving the ultrasonic wave produces an electrical signal corresponding thereto which is transmitted to a received pulse input 48 of the time interval measurement portion of circuit 42. The time interval measurement circuit measures the time interval between the output voltage pulse produced at the output 44 of the pulser circuit portion of circuit 42 and the corresponding received pulse applied to the input 48 of such time measurement circuit in order to determine the time interval of the transient time of the ultrasonic sound wave 46 through the log in a conventional manner. This may be done by a gated pulse oscillator whose output signal is transmitted through a gate to a pulse counter during the time period between when such gate is opened by the transmitted pulse at output 44 and closed by the received pulse at input 48. Other conventional time interval measurement circuits may be used as shown and described in the book "Ultrasonic Measurements For Process Control" by Lawrence C. Lynnworth, published by Academic Press, Inc., in 1989.

It should be noted that the acoustical impedance of a section of the log varies depending upon whether knots or other defects are present within the log section. For example, knots are of higher density than the surrounding wood of the log so that the sound waves travel at a higher velocity through such knots than the surrounding wood. Thus, the transient time interval measured between the time the transmitted ultrasonic pulse is generated by transmitter transducer 38 and the time the received ultrasonic wave is sensed by receiver transducer 40 indicates whether or not internal defects are present in the log.

The time interval signal measured by circuit 42 is supplied to an input 50 of the digital computer 30. The computer 30 determines the acoustical impedance or density along the log and compares it with predetermined acoustical impedance or density information stored in the computer for different species of wood to determine the grade of the log from the time interval signals received at inputs 50 during the scanning of the log. Thus, the transducer wheels 34 and 36 rotate to scan the entire length of the log 14 as it is conveyed in the direction 22 by drive wheels 20, 12. The computer processes the time interval signals together with the log length signal received at input 28 and the log diameter signal received at input 32 to produce a log grade signal and a log volume signal on output terminal 34 which may be transmitted to an analog display device or a printer to produce a permanent record of the log grade together with the log volume for each log tested.

In addition, a log grade indicator signal is produced at output 52 of computer 30 and applied to a color selector circuit 54 which applies a color actuation output signal to one of five solenoid valves 56a, 56b, 56c, 56d, 56e which are each connected to the output of one of five coloring agent reservoirs 58a, 58b, 58c, 58d, 58e respectively containing paint or other liquid coloring agents of different color. The selected solenoid valve opens and causes paint of the proper color to be transmitted through a nozzle 60 onto the rear end 62 of the log to mark such log with a colored paint mark indicating the grade of the log. A solenoid actuated nozzle valve 63 controls the flow of paint through the nozzle 60 and is actuated only after cutting the log end 62 when the chain saw 24 returns to the rest position shown in solid lines in FIG. 1 so that the saw will not be in the way of the paint sprayed from such nozzle.

Figure 2:
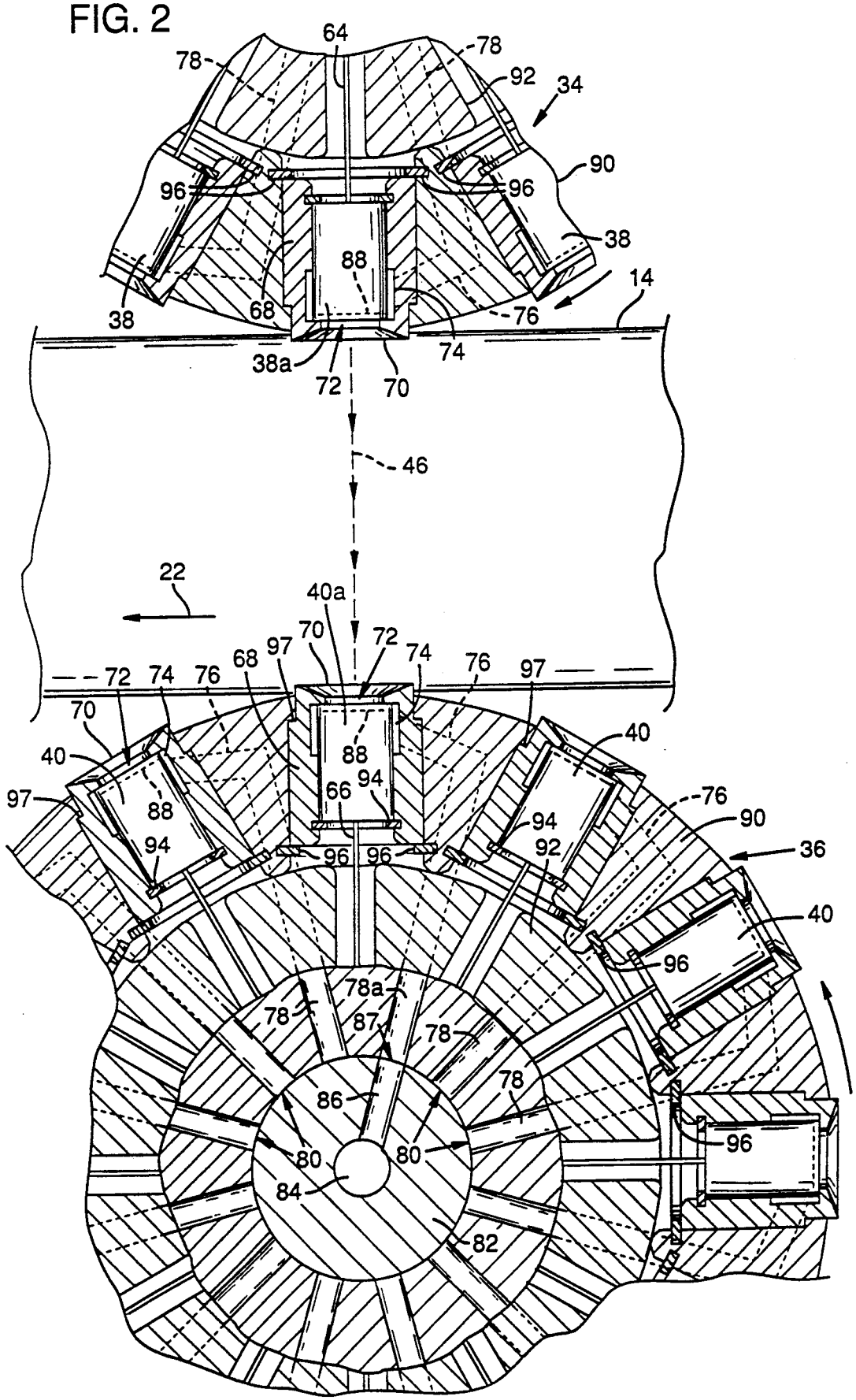
FIG. 2 is an enlarged partial sectional view showing the transducer wheels used to transmit and receive ultrasonic wave energy transmitted through such log as the log is conveyed past such transducer wheels in the apparatus of FIG. 1.

As shown in FIG. 2, the transducer wheels 34, 36 each include a plurality of piezoelectric transducers 38, 40 uniformly spaced about the periphery of such wheels. The piezoelectric transducers 38, 40 are connected by electrical leads 64 and 66, respectively, to the voltage pulse output 44 and the received pulse input 48 of the ultrasonic pulser and time interval measurement circuit 42 of FIG. 1, as well as to any necessary DC bias voltage sources. Each of the transducers 38, 40 is mounted within a cylindrical metal housing 68 having a sharpened outer edge 70 surrounding a fluid coupling chamber 72 of conical shape formed between the output end of the transducer and the log. The fluid coupling chamber 72 communicates with a fluid supply chamber 74 surrounding the transducer 40 formed by a cylindrical groove on the inner wall of the transducer housing 68 and this supply chamber is connected by a fluid passage 76 to one of a plurality of input passages 78 extending through the interior of the transducer wheels 34, 36 which terminate at inlets 80. Thus, there is a different liquid supply passage 76, 78 and associated input opening 80 for each of the fluid chambers 72, 74 surrounding the transducers 38, 40 in order to supply sonic coupling liquid such as water or water and antifreeze into such chambers As a result, the coupling fluid in chamber 72 more efficiently couples the sonic wave between the transducer and the log with less dispersion and attenuation for more efficient operation of the sonic testing apparatus in the transmission of the sonic wave 46 through such log for the detection of internal defects.

The transducer wheels 34, 36 are each rotatably mounted on stationary shafts 82 which have a coupling liquid supply passageway 84 provided through such shaft to a source of coupling liquid such as water for supplying such water through passage 84 and into a connecting output passage 86 extending through the shaft 82 to an outlet opening 87 on the outer surface thereof which is aligned with inlet openings 80 when they are rotated into a discharge position. Thus, there is a single connecting passage 86 which selectively connects one of the coupling liquid passages 78 of each of the transducers on transducer wheels 34, 36 to the coupling liquid supply passage 84 as the coupling liquid chamber 72 associated therewith is rotated into engagement with the log. In the example shown in FIG. 2, only coupling liquid passage 78A which supplies coupling liquid for the transducer 40A is connected through the connecting passage 86 to the liquid supply line 84 at the particular position of rotation of the transducer wheel shown in FIG. 2. However, each of the sonic transducers 40 is connected to the coupling liquid supply line 84 in different angular positions of the transducer wheel 36 once during a full revolution of such wheel, with the liquid coupling connection lasting for a period of rotation of approximately 30°. Thus, there are 12 transducers 40 uniformly spaced 30° apart about the periphery of the wheel. Transducer 40A shown in the vertical position of FIG. 2, is in the center of its 30 degree rotation while the coupling chamber 72 of this transducer begins receiving water into the coupling chamber at a point 15° clockwise from such vertical position and stops receiving water when it has rotated another 15° in a counter-clockwise direction from the vertical position shown. There is a couplant metering groove 88 which connects the liquid supply chamber 74 to the coupling chamber 72 for controlling the flow of liquid from one chamber to another in order to compensate for leakage between the sharp edge 70 of the transducer housing 68 and the log due to the rough surface of the log.

The transducer wheels 34, 36 are both mounted on the stationary shafts 82 by suitable bearings such as tapered roller bearings. Also, it should be noted that the transducer wheels are formed in two releasably connected parts including an outer wheel portion 90 containing cavities for the transducer housings 68 and an inner wheel portion 92 containing fluid passages 78, each wheel portion having overlapping flanges extending from such wheel portions and connected together by drive dowels (not shown). The drive dowels can be removed for disconnecting the transducer wheel portions for disassembly and replacement of the sonic transducers 40 and their housings 68 inside the outer wheel portion 90.

Each transducer module 38, 40 is releasably mounted within their metal housing 68 by split retaining rings 94 of spring steel for easy replacement In addition, retaining rings 96 are provided for retaining the transducer housings 68 within the cavities provided in the outer wheel portion 90 in engagement with a shoulder 97 in such cavity for easy removal of such housings for replacement and repair of the transducers.

Figure 3:
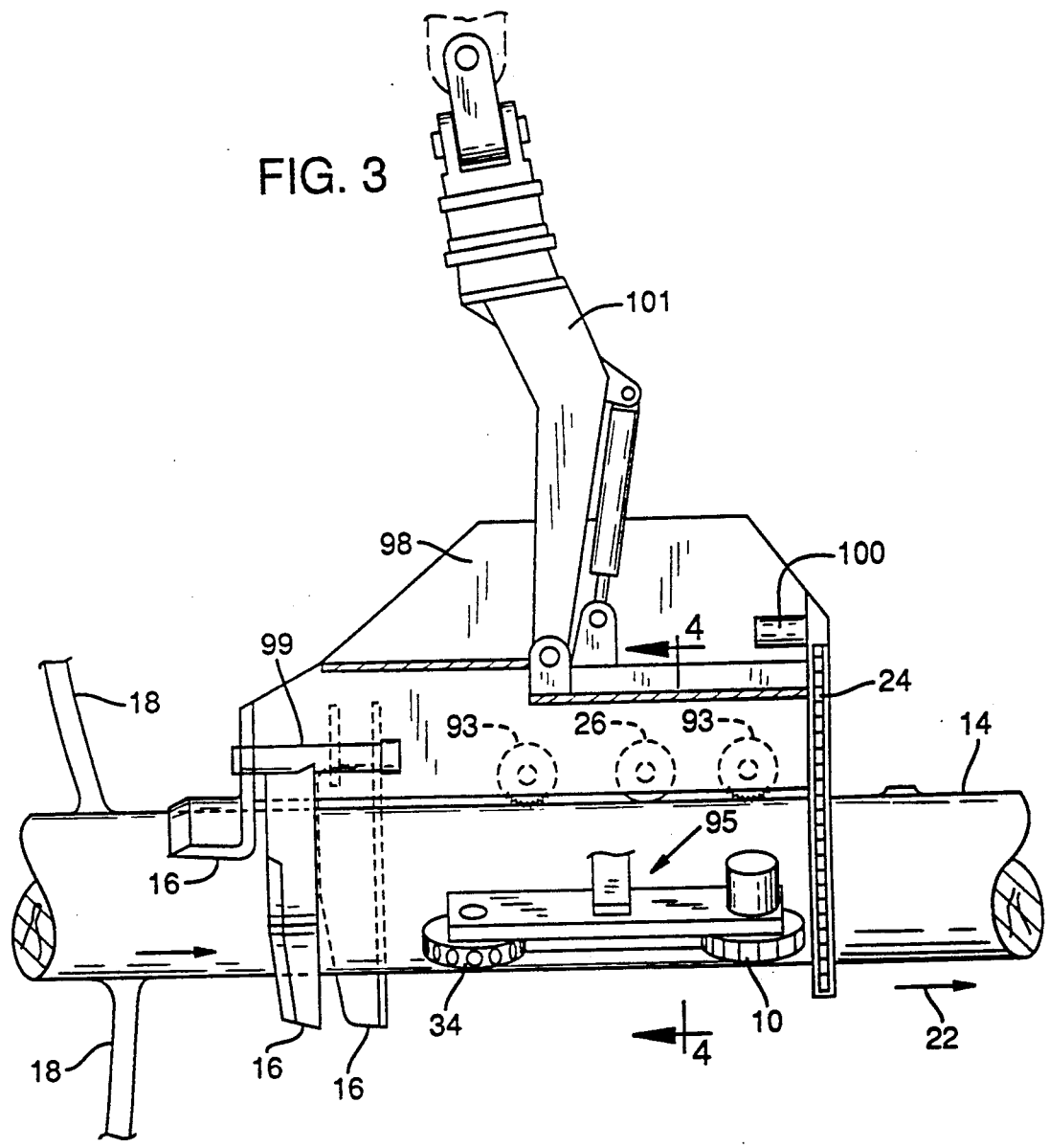
FIG. 3 is a side elevation view showing a tree harvester head in accordance with FIGS. 1 and 2 employing ultrasonic transducer wheels for ultrasonic testing of the log to determine its grade in accordance with the present invention.

It should be noted that electrical connection is made between electrical leads 66 or 64 and the circuit 42 in a conventional manner such as by slip rings and brushes on the shaft 82 and the rotating inner wheel portion 92 so that only one selected pair of transducers 38A and 40A in engagement with the log 14 is energized at one time which may be accomplished by means of a rotating switch having 12 fixed contacts corresponding to each of the transducers and one rotary contact which is coupled to the rotating transducer wheels 34, 36 for rotation therewith As shown in FIGS. 3 and 4, one embodiment of a harvester head 98 connected to the yoke 101 of a hydraulic boom has transducer wheels 34, 36 mounted on moveable supports 95 in common with the drive wheels 10, 12 so that they can be moved into engagement with the outer surface of the log by adjusting the spacing between such transducer wheels to accommodate logs of a different diameter. In this embodiment the transducer wheels 34, 36 whose shafts are pivotally mounted at one end of support arms 102 and 104 which are pivotally mounted on pivots 106 and attached at their opposite ends to a piston rod 108 and a double acting cylinder 110 for moving the transducer wheels into and out of engagement with the log. When the transducer wheels 34, 36 engage the log they are spaced apart approximately 120° or less depending on the diameter of the log as shown in FIG. 4 and are each spaced from the idler wheel 26 also by 120°. The same is true of the drive wheels 10, 12 and such idler wheel 26. As a result the log is captured between three wheels so that it is held in a captive position as it is conveyed longitudinally by the drive wheels 10, 12. The drive wheels are mounted on the same supports 95 for the transducer wheels 34, 36 so that they are also spaced apart by 120° from each other and from the idler wheels 26. Two auxiliary clamp wheels 93 may be provided in line with the idler wheel 26 on opposite sides thereof which need not be driven but function to clamp the log with the drive wheels and transducer wheel for additional stability. Of course the delimbing knives 16 are also mounted on the harvester head 98 by pivots 99 so that they may be adjusted to accommodate different log diameters to remove the limbs 18 from the log before such log is transmitted past the transducer wheels and the drive wheels. In addition, the chain saw 24 is pivotally mounted by a pivot connection 100 to the harvester head 98 so that it may be pivoted into engagement with a tree for felling and with the log produced thereby to cut the log to the proper length to produce the rear end face 62 which is painted to indicate the grade of the log as indicated in FIG. 1.

Another embodiment of the support mechanism for the transducer wheels 34, 36 is shown in FIG. 5 which causes such transducer wheels to be positioned approximately 180° apart so that they are more exactly positioned on opposite sides of the log 14. This may be achieved by scissors-type support arms 102, 104 which are attached at one end to the fixed shafts 82 of transducer wheels 34, 36 respectively and are interconnected by a pivot connection 106. The opposite ends of the support arms 102, 104 are connected to the outer end of a piston rod 108 and the rear end of a cylinder 110 containing such piston by suitable pivot connections. The cylinder may be a double acting cylinder which is controlled by suitable solenoid valves for moving the transducer wheels 34, 36 into contact with logs of different diameter.

It should be noted that while in the preferred embodiment a pair of separate transmitting and receiving transducers are employed for producing an ultrasonic wave which is transmitted completely through the log from one transducer to the other, it is also possible to use a single transducer for both transmitting and receiving the same wave with pulse echo reflection measurement technique. With this technique the same transducer or two different transducers mounted on the same side of the log are employed for testing the log for internal defects. With echo reflection the sound wave is reflected from the wood to air interface on the opposite side of the log from the transducer and is directed back through the log to a receiving transducer or to the sending transducer which then acts as a receiving transducer after the voltage pulse applied thereto has terminated. However, this pulse echo reflection sonic testing technique requires ultrasonic waves of very high intensity and may not be suitable for some logs of large diameter.

In the embodiment shown in FIG. 5, the transducer wheels 34, 36 are each mounted on a stationary shaft 82 which is fixedly attached to the support arms 102, 104 respectfully, but in other ways such transducer wheels operate in a similar manner described above with regard to FIG. 2. Also, in this embodiment it may be preferred to mount the drive wheels 10, 12 independently from the transducer wheels so that the drive wheels form with the idler wheel a captive containment system for the log and are spaced 120° apart and from the idler wheel 26 in the manner previously described with respect to FIG. 4.

It will be obvious to those having ordinary skill in the art that many changes may be made in the above-described preferred embodiments of the invention. Therefore, the scope of the invention should only be determined by the following claims

I claim:
1. A method for testing logs, comprising:
   supporting a log in a test position;
   scanning said log in said test position with ultrasonic wave energy which is produced in response to an electrical input signal and is transmitted into said log;
   detecting said ultrasonic wave after it has been transmitted at least partially through said log;
   producing an electrical output signal corresponding to the detected ultrasonic wave;
   comparing said input signal and said output signal to measure changes in acoustical impedance of said log corresponding to defects in the log; and
   automatically determining the grade of said log from said changes in acoustical impedance.
2. A method in accordance with claim 1 in which the log is moved longitudinally through said test position as it is being scanned along its length with ultrasonic wave energy.
3. A method in accordance with claim 1 in which the scanning ultrasonic wave is generated by electrical input signal pulses and the detected ultrasonic radiation produces corresponding electrical output signal pulses.
4. A method in accordance with claim 3 in which the time delay between said input pulses and each corresponding output pulse is measured to determine changes in acoustical impedance of the log.
5. A method in accordance with claim 1 in which the grade of the log is automatically determined by computer data processing of data signals corresponding to said changes in acoustical impedance and the log is marked with indicia indicating its grade.
6. A method in accordance with claim 1 in which the ultrasonic wave is transmitted into the log through a coupling liquid during scanning of the log.

7. A method in accordance with claim 5 in which the length and diameter of the log are also measured at said test position to produce corresponding test data signals which are also fed to the computer.
8. A method in accordance with claim 1 in which the ultrasonic wave is transmitted through said log from a first transducer on one side of the log to a second transducer on the opposite side of the log which detects said ultrasonic wave.
9. A method in accordance with claim 1 in which the ultrasonic wave is transmitted through said log from a transmitter transducer to a detector transducer on the same side of the log.
10. A method in accordance with claim 9 in which the transmitter transducer and the detector transducer are the same transducer.
11. Apparatus for testing logs, comprising:
   support means for supporting a log in a test position;
   scanner means for scanning said log in said test position with ultrasonic wave energy which is produced in response to an electrical input signal and is transmitted into said log;
   detector means for detecting said ultrasonic wave after it has been transmitted at least partially through said log and for producing an electrical output signal corresponding to the detected ultrasonic wave;
   measurement means for comparing said input signal and said output signal to measure changes in acoustical impedance of said log corresponding to defects in the log; and
   data processor means for automatically determining the grade of said log from said changes in acoustical impedance.
12. Apparatus in accordance with claim 11 in which the support means moves the log longitudinally through said test position as it is being scanned along its length with ultrasonic wave energy.
13. Apparatus in accordance with claim 11 in which the scanner means generates the ultrasonic waves in response to electrical input signal pulses and the detector means produces electrical output signal pulses in response to detected ultrasonic waves.
14. Apparatus in accordance with claim 13 in which the measurement means measures the time delay between said input pulses and each corresponding output pulse to determine changes in acoustical impedance of the log.
15. Apparatus in accordance with claim 11 in which the data processor means is a digital computer means for determining the grade of the log by computer data processing of data signals corresponding to said changes in acoustical impedance and which includes marking means for marking said log with indicia indicating its grade.
16. Apparatus in accordance with claim 11 in which the scanner means and detector means transmit ultrasonic waves into the log through a coupling liquid during scanning of the log.
17. Apparatus in accordance with claim 15 which also includes sensor means for sensing the length and diameter of the log at said test position to produce corresponding test data signals which are also fed to the computer means.
18. Apparatus in accordance with claim 11 in which the ultrasonic wave is transmitted through said log from a first transducer on one side of the log to a second transducer on the opposite side of the log which detects said ultrasonic wave.

19. Apparatus in accordance with claim 11 in which the scanner means and the detector means include a plurality of ultrasonic transducers mounted on a transducer conveyor which moves along the log so that the transducers are selectively coupled to the side of the log during scanning in different positions of said transducer conveyor.

20. Apparatus in accordance with claim 19 in which the transducers are each mounted within a transducer housing having a coupling cavity which is selectively connected to a source of coupling liquid to fill said cavity with coupling liquid and thereby couple the transducer in said housing to the log.

21. Apparatus in accordance with claim 20 in which the transducer housing has a sharp edge surrounding the coupling cavity which projects into engagement with the side of the log.

22. Apparatus in accordance with claim 19 in which the transducer conveyor is a transducer wheel and a plurality of transducers are arrayed about the periphery of the wheel.

23. Apparatus in accordance with claim 22 in which the transducer wheels are mounted on a carriage which also carries log conveyor wheels for moving the log longitudinally past delimbing knives and sensor means for sensing the length and diameter of the log.

24. Apparatus in accordance with claim 11 in which the scanner means and the detector means include transmitting transducers and receiving transducers mounted on the same side of the log.

25. Apparatus in accordance with claim 11 in which the scanner means and the detector means include ultrasonic sonic transducers which each transmit an ultrasonic wave into the log and detect the ultrasonic wave after it is transmitted through said log.

26. Apparatus for processing logs, comprising:
harvesting head means for gripping and sawing a tree until it is felled to produce a log and for sawing the other end of the log to the proper length;
delimbing means for cutting limbs from said log;
conveyor means for conveying the log through said delimbing means to remove limbs and provide a delimbed log;
scanner means for scanning the delimbed log with ultrasonic wave energy as it is being conveyed to detect internal defects in the log and for producing electrical scan data signals corresponding thereto; and
measurement means for determining the grade of the log from said scan data signals and for marking the log to indicate said grade on the log.

27. Apparatus in accordance with claim 26 in which the scanner means transmits the ultrasonic wave energy completely through the log from one side to its opposite side.

28. Apparatus in accordance with claim 26 in which the ultrasonic wave energy is transmitted into the log through a coupling liquid.

29. Apparatus in accordance with claim 26 which also includes sensor means for sensing the length and diameter of the log as it is being conveyed and producing electrical sensor data signals corresponding thereto.

30. Apparatus in accordance with claim 26 in which the measurement means includes a digital computer means for processing the data signals.

* * * * *

UNITED STATES PATENT AND TRADEMARK OFFICE
CERTIFICATE OF CORRECTION

PATENT NO. : 5,097,881

DATED : March 24, 1992

INVENTOR(S) : Michael J. Mack

It is certified that error appears in the above-identified patent and that said Letters Patent is hereby corrected as shown below:

On the title page:
[57] Line 3, "utlrasonic should be --ultrasonic--;

Column 1, line 18, "that" should be --than--;

Column 1, line 51, "Apr/" should be --Apr.--;

Column 2, line 33 and 34, "delimbing knives" should be --delimbing knives--;

Column 4, line 8, "on" should be --one--;

Column 4, line 67, "output 34" should be --output 33--;

Column 6, line 16, "20, 12" should be --10, 12--;

Column 6, line 20, "terminal 34" should be --terminal 33--;

Column 6, line 65, "chambers As" should be --chambers. As--;

Column 7, line 58, "replacement In" should be --replacement. In--;

Column 9, line 18, "respectfully" should be --respectively--;

UNITED STATES PATENT AND TRADEMARK OFFICE
CERTIFICATE OF CORRECTION

PATENT NO. : 5,097,881
DATED : March 24, 1992
INVENTOR(S) : Michael J. Mack

It is certified that error appears in the above-identified patent and that said Letters Patent is hereby corrected as shown below:

Column 10, line 5, claim 8, "claim I" should be --claim 1--;

Column 10, line 39, claim 12, "energy.," should be --energy.--;

Column 11, line 34, column 12, line 1, claim 25, "ultrasonic sonic" should be --ultrasonic--.

Signed and Sealed this

Twenty-eighth Day of September, 1993

Attest:

BRUCE LEHMAN

*Attesting Officer*      *Commissioner of Patents and Trademarks*